(12) United States Patent
Kim et al.

(10) Patent No.: US 12,383,412 B2
(45) Date of Patent: Aug. 12, 2025

(54) SURGICAL INSTRUMENT AND METHOD

(71) Applicant: WARSAW ORTHOPEDIC INC., Warsaw, IN (US)

(72) Inventors: Abel Kim, Cordova, TN (US); Jonathan M. Dewey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 136 days.

(21) Appl. No.: 18/332,121

(22) Filed: Jun. 9, 2023

(65) Prior Publication Data

US 2023/0310178 A1 Oct. 5, 2023

Related U.S. Application Data

(63) Continuation of application No. 16/855,336, filed on Apr. 22, 2020, now Pat. No. 11,696,839.

(51) Int. Cl.
| | | |
|---|---|---|
| *A61F 2/46* | (2006.01) | |
| *A61B 34/20* | (2016.01) | |
| *A61B 90/00* | (2016.01) | |
| *A61F 2/30* | (2006.01) | |

(52) U.S. Cl.
CPC ............ *A61F 2/4611* (2013.01); *A61B 34/20* (2016.02); *A61B 2034/2051* (2016.02); *A61B 2034/2063* (2016.02); *A61B 2034/2072* (2016.02); *A61B 2090/3764* (2016.02); *A61F 2002/3008* (2013.01); *A61F 2002/4632* (2013.01); *A61F 2310/00023* (2013.01)

(58) Field of Classification Search
CPC .................................................. A61F 2/4611
See application file for complete search history.

(56) References Cited

U.S. PATENT DOCUMENTS

| | | |
|---|---|---|
| 2004/0153080 A1 | 8/2004 | Dong et al. |
| 2005/0021043 A1 | 1/2005 | Jansen et al. |
| 2018/0311051 A1 | 11/2018 | Donaldson et al. |

FOREIGN PATENT DOCUMENTS

| | | |
|---|---|---|
| WO | 2000064367 A1 | 11/2000 |
| WO | 2018057052 A2 | 3/2018 |

OTHER PUBLICATIONS

PCT International Search Report Korean Intellectual Property Office, 189 Cheongsa-ro, Seo-gu, Daejeon 35208, Republic of Korea; International application No. PCT/US2021/023468; International filing date Mar. 22, 2021; Date of mailing of the international search report Jul. 13, 2021.

PCT Written Opinion of the International Searching Authority, Korean Intellectual Property Office, 189 Cheongsa-ro, Seo-gu, Daejeon 35208, Republic of Korea; International application No. PCT/US2021/023468; International filing date Mar. 22, 2021; Date of mailing Jul. 13, 2021.

*Primary Examiner* — Andrew Yang
(74) *Attorney, Agent, or Firm* — Sorell, Lenna & Schmidt, LLP

(57) ABSTRACT

A surgical instrument comprises a member defining a longitudinal axis and being connectable with a spinal implant. A handle is connected with the member. An image guide is connected with the member for orientation relative to a sensor to communicate a signal representative of a position of the spinal implant. The image guide is rotatable about the axis relative to the member and is disposable in at least one fixed position with the member. Systems, implants, spinal constructs and methods are disclosed.

20 Claims, 13 Drawing Sheets

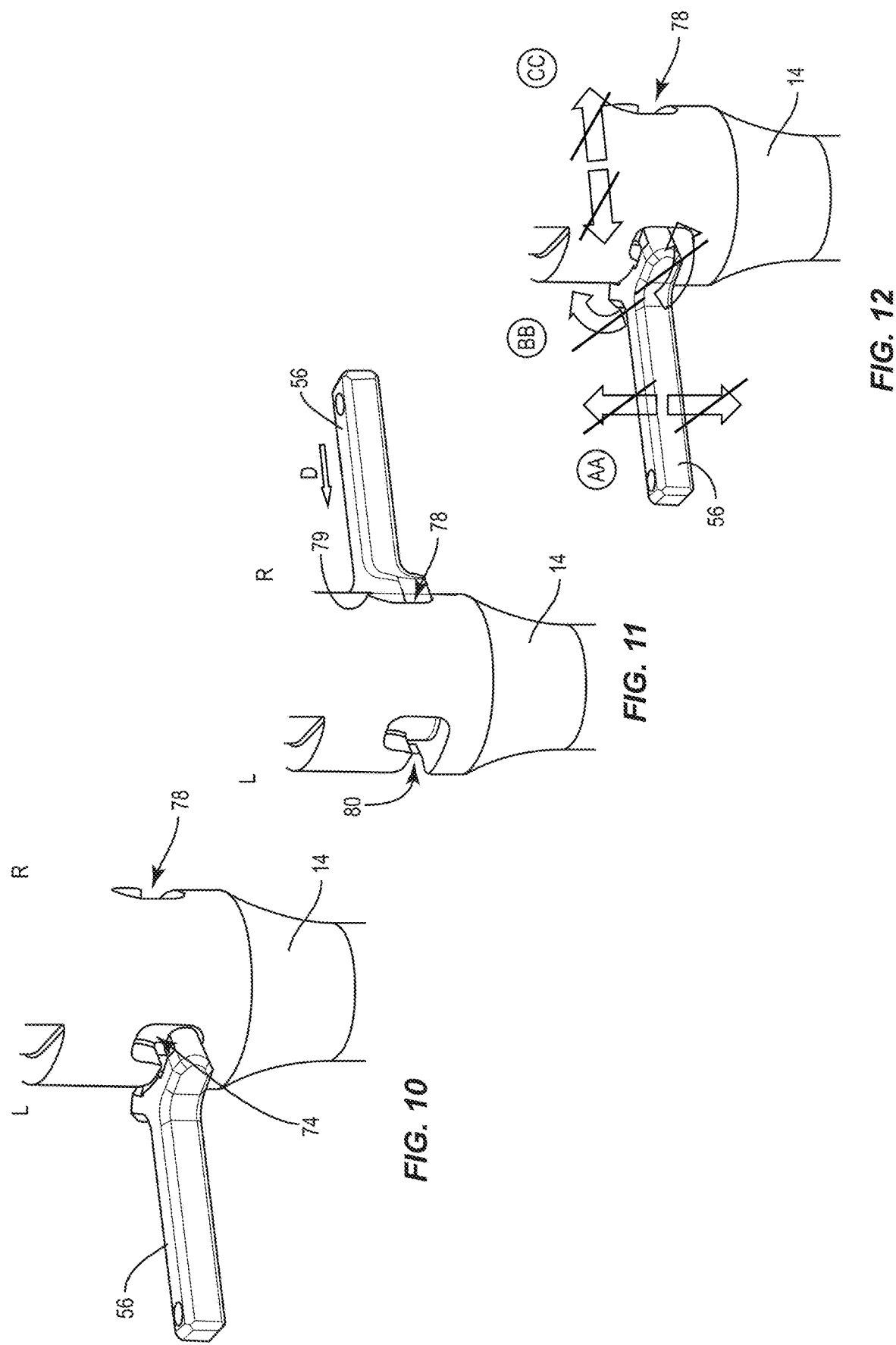

SURGICAL INSTRUMENT AND METHOD

CROSS REFERENCE TO RELATED APPLICATIONS

This application is a continuation of U.S. patent application Ser. No. 16/855,336, filed Apr. 22, 2020, which is expressly incorporated by reference herein, in its entirety.

TECHNICAL FIELD

The present disclosure generally relates to medical devices for the treatment of musculoskeletal disorders, and more particularly to a surgical system and a method for treating a spine.

BACKGROUND

Spinal pathologies and disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, corpectomy, discectomy, laminectomy and implantable prosthetics. For example, fusion and fixation treatments may be performed that employ implants to restore the mechanical support function of vertebrae. Surgical instruments are employed, for example, to prepare tissue surfaces for disposal of the implants. Surgical instruments are also employed to engage implants for disposal with the tissue surfaces at a surgical site. This disclosure describes an improvement over these prior technologies.

SUMMARY

In one embodiment, a surgical instrument is provided. The surgical instrument comprises a member defining a longitudinal axis and being connectable with a spinal implant. A handle is connected with the member and an image guide is connected with the member for orientation relative to a sensor to communicate a signal representative of a position of the spinal implant. The image guide is rotatable about the axis relative to the member and disposable in at least one fixed position with the member. In some embodiments, surgical systems, implants, spinal constructs and methods are provided.

In one embodiment, the surgical instrument comprises a shaft that defines a longitudinal axis and is connectable with a spinal implant. The shaft is connected to a handle disposed transverse relative to the axis. An actuator is connected with the shaft and the handle. An image guide is connected with the shaft and oriented relative to a sensor to communicate a signal representative of a position of the spinal implant. The image guide is rotatable about the axis relative to the shaft and the actuator is configured to dispose the image guide between a fixed position and a non-fixed position with the shaft.

In one embodiment, a surgical system is provided. The surgical system comprises a spinal implant. A surgical instrument is connectable with the spinal implant. The surgical instrument includes a member defining a longitudinal axis and a handle being disposed transverse relative to the axis. An actuator is connected with the member and the handle. An image guide is connected with the shaft and oriented relative to a sensor to communicate a signal representative of a position of the spinal implant. The image guide is rotatable about the axis relative to the shaft and the actuator is configured to dispose the image guide between a fixed position and a non-fixed position with the shaft. A tracking device includes the sensor that receives the signal and communicates with a processor to generate data for display of an image from a monitor. The image represents a position of the spinal implant relative to tissue.

BRIEF DESCRIPTION OF THE DRAWINGS

The present disclosure will become more readily apparent from the specific description accompanied by the following drawings, in which:

FIG. 10 is a perspective view of components of the surgical system shown in FIG. 8;

FIG. 11 is a perspective view of components of the surgical system shown in FIG. 8;

FIG. 12 is a perspective view of components of the surgical system shown in FIG. 8;

DETAILED DESCRIPTION

Figure 1:
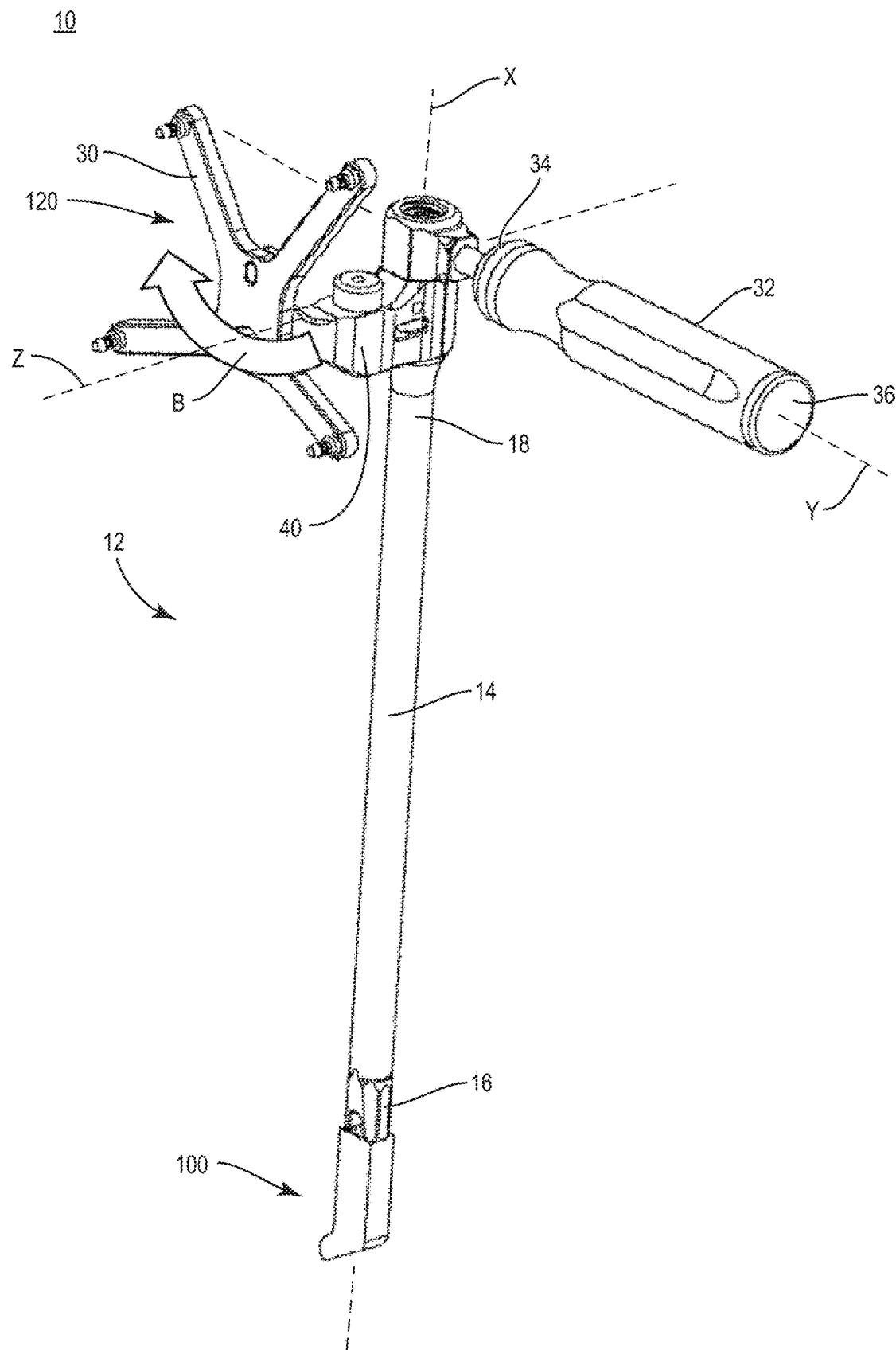
FIG. 1 is a perspective view of components of one embodiment of a surgical system in accordance with the principles of the present disclosure.

The exemplary embodiments of a surgical system are discussed in terms of medical devices for the treatment of musculoskeletal disorders and more particularly, in terms of a surgical system for preparing a surgical site, and a method for treating a spine. In some embodiments, the present surgical system includes a surgical instrument comprising an interbody inserter for use with a surgical navigation system for placement of an interbody device. In some embodiments, the inserter includes an image guide, for example, a tracker and a distal tip configured for engagement with an implant, for example, a spinal implant.

In some embodiments, the present surgical system includes a surgical instrument having a tracker that is rotatable for orientation relative to a sensor of a surgical navigation system to communicate a signal representative of a position of a spinal implant. In some embodiments, the tracker is optically tracked and is disposed in a line-of-sight view to a sensor, for example, a camera. In some embodiments, the tracker provides a location of the surgical instrument in three dimensions. In some embodiments, the tracker provides a location of the surgical instrument and/or a spinal implant in two dimensions, for example, a selected plane. In some embodiments, this configuration provides indicia and/or display of implant position corresponding to an amount of manipulation, movement, translation and/or rotation of a spinal implant with tissue.

In some embodiments, the present surgical system includes a surgical instrument, for example, an implant inserter having a surgical navigation tracker. In some embodiments, the navigating tracker is disposed on a shaft of the inserter and is rotatable relative to the shaft. In some embodiments, the present surgical system includes an interbody implant, for example, a biased implant and the tracker is rotatable into a selected orientation such that the tracker is aligned with the sensor and the surgical instrument does not have to be removed from the surgical site. In some embodiments, the tracker is disposed in an incorrect initial orientation relative to the camera and the tracker is rotatable relative to a shaft of a surgical instrument to a correct orientation such that the tracker is aligned with the sensor and the surgical instrument does not have to be removed from the surgical site. In some embodiments, the present surgical system includes a surgical instrument having a surgical navigation tracker and an actuator that facilitates adjusting position of the tracker relative to the surgical instrument from one side of the surgical instrument to another side of the surgical instrument.

In some embodiments, the present surgical system includes a surgical instrument, for example, an implant inserter having a surgical navigation tracker and is employed with a method including the step of rotating the navigation tracker to adjust its orientation relative to the implant inserter. In some embodiments, the tracker rotates from one side of the inserter to a second side of the inserter. In some embodiments, the method includes a surgical procedure, and if an incorrect orientation of the tracker is initially selected, the tracker can be rotated into a correct orientation on the inserter such that the tracker can maintain its alignment with a camera. In some embodiments, the present surgical system includes an implant inserter having a surgical navigation tracker that is configured to reduce error that occurs when the tracker is not detected by the camera during a surgical procedure or due to miscommunication with surgical staff. In some embodiments, the present surgical system includes a surgical instrument, for example, an implant inserter having a surgical navigation tracker and an actuator, for example, a button. In some embodiments, the implant inserter has a surgical navigation tracker and is employed with a method including a surgical procedure comprising the step of engaging an actuator including a button. In some embodiments, the step of engaging includes disposing the actuator in a non-locked position such that the tracker can be rotated and positioned into a selected orientation relative to the inserter and/or a sensor. In some embodiments, the method includes the step of releasing the actuator for disposal in a locked position such that the tracker is locked in a selected orientation. In some embodiments, during a surgical procedure, the inserter and/or a surgical navigation system includes indicia corresponding to the tracker orientation change and the surgical procedure can proceed.

In some embodiments, the present surgical system includes a surgical instrument, for example, an implant inserter having a surgical navigation tracker with an actuator, for example, a button, a pin, and a biasing member, for example, a spring. In some embodiments, the pin includes a Y shaped configuration and includes a first arm and a second arm. In some embodiments, each arm includes an end having a surface that defines a peg. In some embodiments, the shaft of the inserter includes a surface that defines transverse slots. In some embodiments, the slots are configured for engagement with the pegs of the pin. In some embodiments, to rotate the tracker, the button is depressed in a direction to disengage the pegs from the slots. In some embodiments, the tracker is rotated. In some embodiments, as the tracker is rotated, the pegs slide through a clearance slot such that the tracker can be rotated into another position.

In some embodiments, the present surgical system includes a surgical instrument, for example, an implant inserter having the pin and the slots of the shaft being rigidly connected. In some embodiments, the connection between the pin and the shaft increases accuracy and/or integrity of the tracker connection with the surgical instrument relative to a spinal implant. In some embodiments, the slots include a tapered or converging configuration and the ends of the arms of the pin converge such that the slots and the pin rigidly connect. In some embodiments, the tapered or converging configuration of the slots and the tapered or converging configuration of the pin include a dual taper between the slots and the pin to reduce movement or play between the slots and the pin in a locking configuration or a fully seated condition.

In some embodiments, the present surgical system includes a surgical instrument, for example, an implant inserter having an actuator including a button that is released and the pin translates upward, spring forces of the button force the dual taper to draw the pin into the slots of the inserter. In some embodiments, the dual taper resists axial movement along an axis of the shaft. In some embodiments, the dual taper resists tangential movement around the shaft. In some embodiments, the dual taper resists radial movement in and out of the shaft. In some embodiments, when the button disengages with the pin, the pin is movable and/or configured to float in the button to facilitate relative movement. In some embodiments, the button engages the pin, and the spring force of the button pushes angled faces of the button against the pin to resist relative movement or play between the components.

In some embodiments, the present surgical system includes a surgical instrument, for example, an implant inserter having a surgical navigation tracker that is rotatable in multiple orientations relative to the inserter. In some embodiments, the tracker can include a ball such that the tracker can be relatively positioned in multiple orientations on the shaft of the inserter for alignment with the camera. In some embodiments, the inserter can include two trackers such that a processor and/or software implemented with a surgical navigation system can identify the location of the tracker relative to the inserter shaft, for example, to determine a side of the inserter shaft that the tracker is located. In some embodiments, the tracker can be fixed and/or locked into an orientation by detents, a threaded locking collar, and/or a sliding or pivoting pin or pins.

In some embodiments, the present surgical system includes a surgical instrument, for example, an implant inserter having a shaft that includes a distal tip being engageable with a spinal implant, for example, a biased interbody implant. In some embodiments, the implant engages the distal tip of the inserter in only one orientation. In some embodiments, the distal tip includes a protrusion on a single side. In some embodiments, an end of the implant includes a groove on a single side. In some embodiments, the groove has a dedicated and/or specific mating configuration with the protrusion and the groove engages the protrusion for mated engagement. In some embodiments, if a user attempts to engage the distal tip with the implant in error, an incorrect orientation and/or a non-selected implant, the protrusion engages a non-dedicated and/or non-specific mating surface, for example, a side of the implant that does not include a groove, and as such, mating engagement between the distal tip and the implant is prevented.

In some embodiments, the present surgical system includes a spinal implant having a tip, for example, a biased tip. In some embodiments, the implant includes a sloped tip. In some embodiments, the tip protrudes and is wider than a main body of the implant. In some embodiments, the present tip configuration avoids inserting an implant into a surgical space in a non-selected orientation, for example, an intervertebral disc space with the tip pointing in a non-selected direction. In some embodiments, the present tip configuration facilitates disposal of the tip in a selected direction or orientation, for example, the tip including an end of the implant extending parallel to an anterior rim of an intervertebral disc to distribute loads on the spine. In some embodiments, the present tip configuration avoids inserting an implant into a surgical space in an incorrect orientation, for example, an end of the implant projecting from a front of an intervertebral disc space and concentrating vertebral loading. In some embodiments, the implant is capable of expanding unilaterally.

In some embodiments, the present surgical system includes a processor for executing a software program. In some embodiments, the processor executes the software program with a computer display that includes an implant tip configuration menu that allows a user to select a tip of an inserter, and the processor communicates with a computer display to indicate the actual tip being implemented by the inserter. In some embodiments, the inserter includes indicia, for example, a letter, number and/or shape, which indicates the type of implant orientation being employed. In some embodiments, the processor communicates with a computer display and implements the same indicia used on the inserter such that the inserter indicia and the computer display indicia match. In some embodiments, the processor and computer display are coordinated with a direction of the tracker. In some embodiments, the processor and the computer display include a surface implant menu that includes a tip style, height of implant, length of implant and tip configuration.

In some embodiments, the present surgical system includes a surgical instrument, for example, an implant inserter employed with a method of using a navigation system in navigated spine procedures. In some embodiments, the surgical instrument can be employed with optical-based navigation systems to facilitate surgical instrument line of sight between an instrument rotating tracker and a camera. In some embodiments, this configuration facilitates the ability to consistently track surgical instrument position throughout a surgical procedure in connection with location of a navigation camera in an operating room and for patient positioning.

In some embodiments, the present surgical system includes a surgical instrument that has an instrument rotating tracker and a distal/working end. In some embodiments, the surgical tracker provides indicia and/or display of a location and angulation of the surgical instrument and its distal/working end. In some embodiments, the surgical system includes a surgical instrument having one or more image guides, which include one or more fiducial markers. In some embodiments, the fiducial marker includes a single ball-shaped marker. In some embodiments, the image guide is disposed adjacent a proximal end of the surgical instrument. In some embodiments, the image guide provides indicia and/or display of a precise rotational and/or linear position of the image guide on the surgical instrument. In some embodiments, this configuration provides indicia and/or display of an amount of manipulation, movement, translation and/or rotation of the implant with tissue.

In some embodiments, the surgical instrument includes a navigation rotating tracker and is disposed in a direct line of sight of a sensor, which includes one or more cameras. In some embodiments, the surgical system includes an O-arm medical imaging device that digitally captures images of an anatomy. In some embodiments, the tracker communicates with a surgical navigation system to determine and/or display surgical instrument positioning relative to the anatomy.

In some embodiments, one or all of the components of the surgical system may be disposable, peel pack and/or pre packed sterile devices. One or all of the components of the surgical system may be reusable. The surgical system may be configured as a kit with multiple sized and configured components.

In some embodiments, the surgical system of the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the surgical system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

The following discussion includes a description of a surgical system including surgical navigation, a surgical instrument, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-24, there are illustrated components of a surgical system 10.

The components of surgical system 10 can be fabricated from biologically acceptable materials suitable for medical applications, including metals, synthetic polymers and/or ceramics. For example, the components of surgical system 10, individually or collectively, can be fabricated from materials such as stainless steel alloys, aluminum, commercially pure titanium, titanium alloys, Grade 5 titanium, super-elastic titanium alloys, cobalt-chrome alloys, super-elastic metallic alloys (e.g., Nitinol, super elasto-plastic metals, such as GUM METAL®), ceramics, thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene and/or epoxy.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with a fully open surgical procedure, a minimally invasive procedure including percutaneous techniques, and mini-open surgical techniques to deliver and introduce instrumentation and/or one or more implants at a surgical site within a body of a patient, for example, a section of a spine. In some embodiments, the surgical instrument can be configured to deliver and introduce one or more components of a spinal construct, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Surgical system 10 includes a surgical instrument, for example, an inserter 12. Inserter 12 includes a member, for example, a shaft 14. Shaft 14 extends between an end 16 and an end 18 and defines a longitudinal axis X, as shown in FIG. 1. End 16 includes an engagement portion 20 configured for engagement with an interbody implant 100, as described herein. End 18 is connected with an image guide, for example, a navigation component 30 and a handle 32, as described herein.

Handle 32 includes an end 34 and an end 36, and defines an axis Y. Handle 32 extends between ends 34, 36 transverse to shaft 14. In some embodiments, handle 32 may be disposed at alternate orientations relative to shaft 14, for example, parallel, perpendicular and/or other angular orientations such as acute or obtuse, co-axial, offset, and/or staggered. In some embodiments, handle 32 may include alternate surface configurations to enhance gripping of handle 32, for example, rough, arcuate, undulating, mesh, porous, semi-porous, dimpled and/or textured. In some embodiments, handle 32 may include alternate cross section configurations, for example, oval, oblong, triangular, square, hexagonal, polygonal, irregular, uniform, non-uniform and/or tapered.

Navigation component 30 is rotatable about longitudinal axis X relative to shaft 14, in the direction shown by arrow B in FIG. 1 and is disposable in a movable, non-fixed and/or non-locking state such that navigation component 30 is rotatable relative to shaft 14 to a selected and non-movable, fixed and/or locking state to orient navigation component 30 for alignment and detection of a signal with a sensor, for example, a sensor array 202 of a navigation system 200. In some embodiments, the non-movable, fixed and/or locking state creates a rigid fixation or connection between navigation component 30 and shaft 14 to increase accuracy and/or integrity of the navigation component 30 connection with shaft 14. In some embodiments, during a surgical procedure, if navigation component 30 is initially incorrectly oriented, disposed in a non-selected position and/or disposed in a non-aligned orientation relative to sensor array 202, navigation component 30 is rotatable into a selected and/or aligned orientation, for example, a left side L or a right side R of inserter 12 such that navigation component 30 is correctly oriented and aligned with sensor array 202, thereby avoiding the step of removing inserter 12 from the surgical site. In some embodiments, navigation component 30 is rotatable to reduce error that occurs when navigation component 30 is not detected by the sensor array 202 during a surgical procedure or due to miscommunication with surgical staff.

Figure 2:
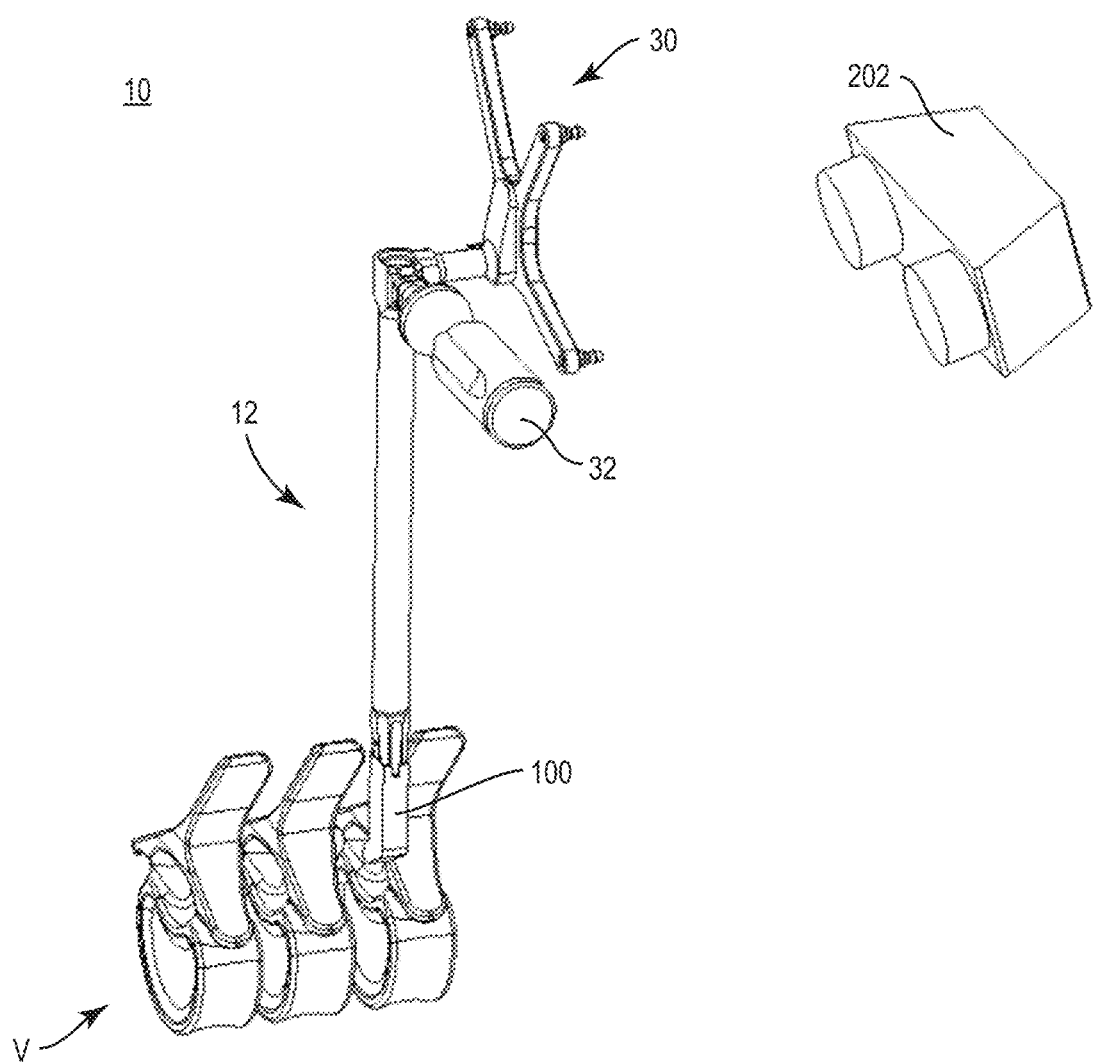
FIG. 2 is a perspective view of components of one embodiment of a surgical system in accordance with the principles of the present disclosure disposed with vertebrae.

Navigation component 30 is attached with end 18 at a selected distance from one or more components of inserter 12 and/or implant 100 connected with inserter 12 to represent position and/or orientation of one or more components of inserter 12, implant 100 and/or tissue, as described herein. Inserter 12 is configured for disposal adjacent a surgical site such that navigation component 30 is oriented relative to sensor array 202 to facilitate communication between navigation component 30 and sensor array 202, as shown in FIG. 2 during a surgical procedure, as described herein.

Navigation component 30 defines a longitudinal axis Z and includes an arm 38 configured for engagement with an actuator 40, as shown in FIGS. 1 and 5-7. Actuator 40 is connected with shaft 14 and navigation component 30, and is configured to dispose navigation component 30 between the movable, non-fixed and/or non-locking state and the non-movable, fixed and/or locking state relative to shaft 14. Actuator 40 includes a wall 42 having a surface that defines an opening 44 configured for disposal of arm 38. Arm 38 is at least partially threaded. In some embodiments, arm 38 and/or opening 44 is variously configured, for example, smooth, rough, arcuate, undulating, mesh, porous, semi-porous, dimpled and/or textured. In some embodiments, arm 38 may include alternate cross section configurations, for example, oval, oblong, triangular, square, hexagonal, polygonal, irregular, uniform, non-uniform and/or tapered. In some embodiments, navigation component 30 is connected with actuator 40 via an integral connection, friction fit, pressure fit, interlocking engagement, mating engagement, dovetail connection, clips, barbs, tongue in groove, threaded, magnetic, key/keyslot and/or drill chuck.

In some embodiments, navigation component 30 is configured to spin or rotate about axis Z to avoid interference with the patient and/or to orient navigation component 30 for alignment with sensor array 202. In some embodiments, navigation component 30 is slidable relative to shaft 14 such that navigation component 30 is movable in an inward or an outward direction relative to axis X. In some embodiments, navigation component 30 is slidable and can be moved in close proximity to implant 100 to increase accuracy and/or to accommodate the size of the patient, including, for example, a patient that is a normal body weight or is underweight. In some embodiments, navigation component 30 is slidable and can be moved in an inward or outward direction relative to axis X to accommodate the size of a patient and/or to orient navigation component 30 for alignment with sensor array 202.

Figure 5:
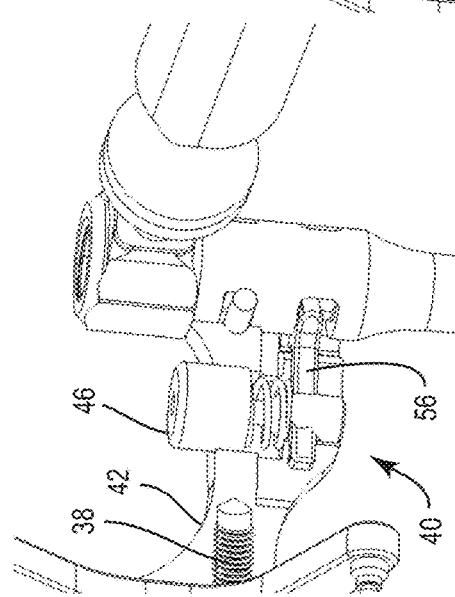
FIG. 5 is a cutaway view of components of the surgical system shown in FIG. 1.
Figure 6:
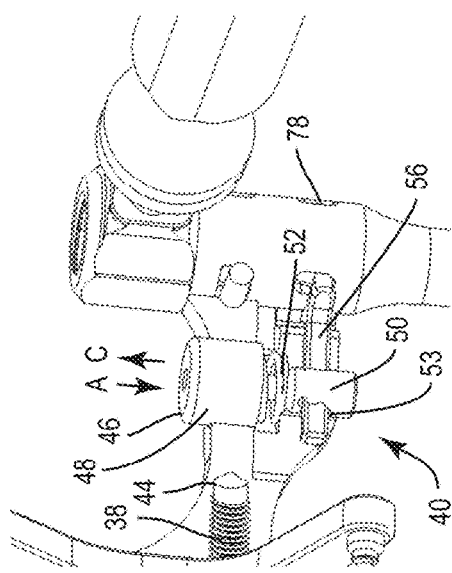
FIG. 6 is a cutaway view of components of the surgical system shown in FIG. 1.
Figure 7:
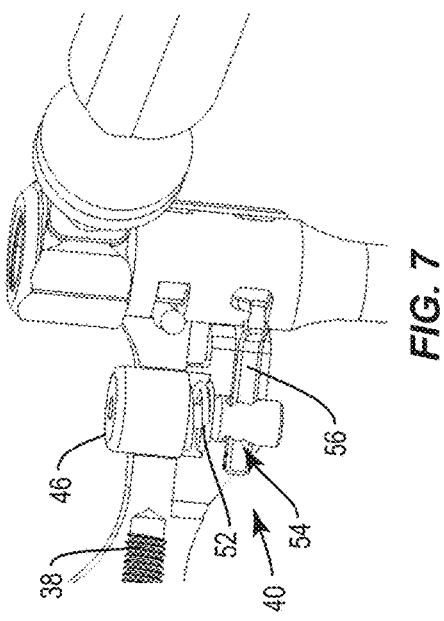
FIG. 7 is a cutaway view of components of the surgical system shown in FIG. 1.
Figure 9:
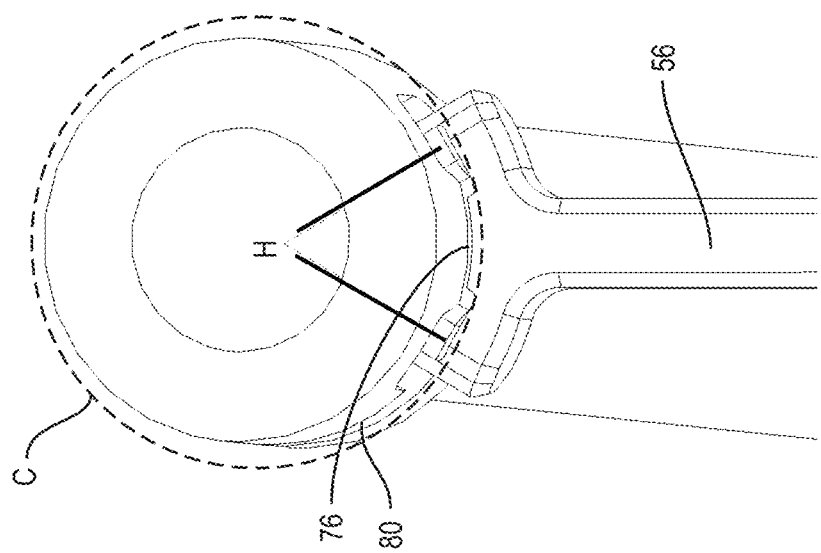
FIG. 9 is a perspective view of components of the surgical system shown in FIG. 8.

Actuator 40 includes a button 46. Button 46 includes a proximal end 48 and a distal end 50. A spring 52 is disposed about end 50. When spring 52 is disposed in an expanded position, spring 52 applies a force to button 46 such that button 46 is resiliently biased into the non-movable, fixed and/or locking state, as shown in FIG. 6. As such, button 46 is spring loaded into the non-movable, fixed and/or locking state. When a force is applied to button 46, for example via manual engagement, the force overcomes the force applied by spring 52 causing button 46 to translate navigation component 30 into the movable, non-fixed and/or non-locking state, as shown in FIGS. 1 and 7. Button 46 includes an inner surface 53 that defines a cavity 54 configured for disposal of a transverse pin 56, as shown in FIGS. 5-7. Cavity 54 is transverse relative to axis X. In some embodiments, cavity 54 may be disposed at alternate orientations relative to axis X, for example, perpendicular and/or other angular orientations such as acute or obtuse, co-axial, offset, and/or staggered. In some embodiments, button 46 can be variously configured, for example, lever, square, rectangular, or domed shaped.

Figure 4:
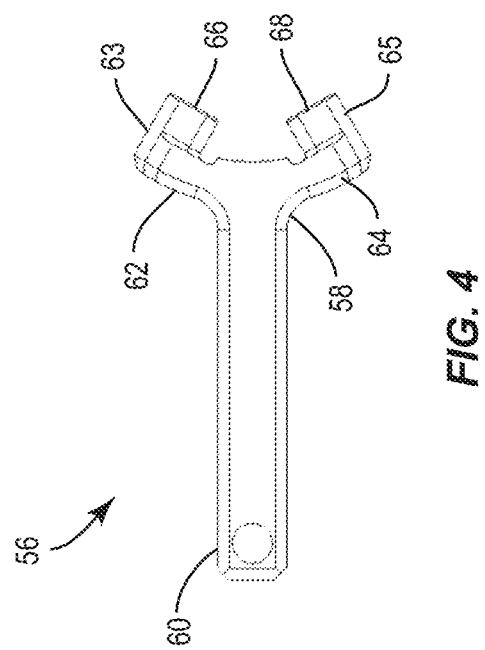
FIG. 4 is a plan view of components of the surgical system shown in FIG. 3.
Figure 3:
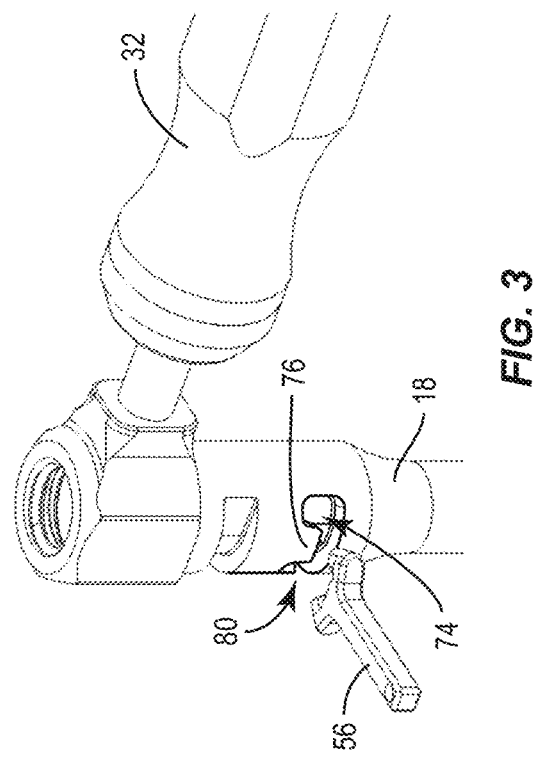
FIG. 3 is a break away view of the components of the surgical system shown in FIG. 1 with parts separated.

Pin 56 is configured for disposal with button 46 and shaft 14. Pin 56 includes a proximal end 58 and a distal end 60, as shown in FIG. 4. A portion of end 60 is in a flush engagement with surface 53 creating a rigid fixation such that button 46 facilitates movement of pin 56, as described herein. End 58 includes bifurcated arms 62, 64 that are disposed in a Y shaped configuration. Arm 62 includes a surface 63 that defines a peg 66 and arm 64 includes a surface 65 that defines a peg 68. Pegs 66 and 68 are angled relative to each other. Pegs 66, 68 are in a tapered or converging configuration relative to each other, indicated by lines H in FIG. 9, and are configured for engagement with shaft 14, as described herein. In some embodiments, pin 56 can include 1 to 4 pegs. In some embodiments, each arm 62, 64 can include 1 to about 4 pegs. In some embodiments, pegs 66, 68 alternatively include spikes, pins, nails, dowels, rivets, and/or teeth. In some embodiments, pegs 66, 68 may include surface configurations to enhance engagement with shaft 14, for example, smooth, rough, arcuate, undulating, mesh, porous, semi-porous, dimpled and/or textured. In some embodiments, pin 56 may be disposed at alternate orientations relative to shaft 14, for example, parallel, and/or other angular orientations such as acute or obtuse, co-axial, offset, and/or staggered.

Figure 8:
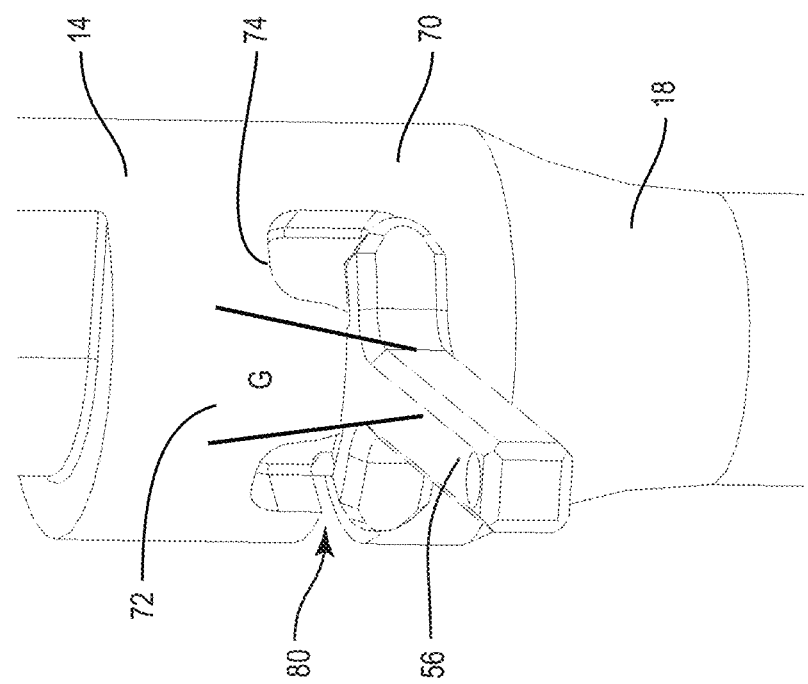
FIG. 8 is a break away perspective view of components of one embodiment of a surgical system in accordance with the principles of the present disclosure in cutaway.
Figure 14:
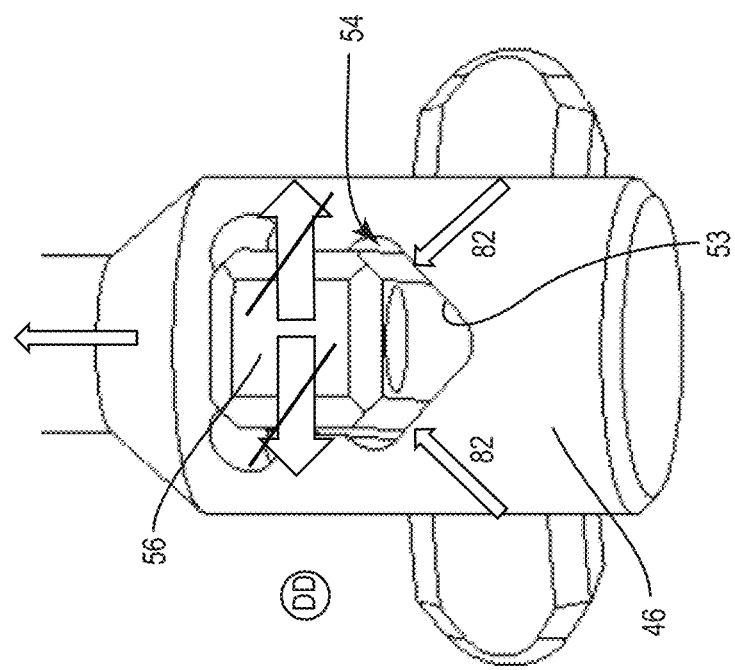
FIG. 14 is a plan view of the components of the surgical system shown in FIG. 13.

End 18 includes a surface 70 that defines a wall 72, as shown in FIG. 8. Wall 72 defines a transverse slot 74, a transverse slot 78, and a circumferential slot 80 configured to connect slot 74 and slot 78, as shown in FIGS. 8-11. Slot 78 is diametrically disposed about a circumference C of shaft 14 relative to slot 74. Slots 74 and 78 are configured for engagement with pin 56 to orient navigation component 30 in the non-movable, fixed and/or locking state on the left side L and the right side R of shaft 14 for alignment and detection of a signal with a sensor, for example, sensor array 202 of navigation system 200. In some embodiments wall 72 defines a plurality of slots to facilitate a plurality of fixed and/or locking states.

In the fixed and/or locking state, navigation component 30 is rigidly fixed with shaft 14 due to a rigid connection between pin 56 and slot 74, as described herein. In some embodiments, slot 74 is variously configured, for example, smooth, rough, arcuate, undulating, mesh, porous, semi-porous, dimpled and/or textured. In some embodiments, slot 74 may include alternate cross section configurations, for example, oval, oblong, triangular, square, hexagonal, polygonal, irregular, uniform, non-uniform and/or tapered.

Wall 72 defines a projection 76 disposed in slot 74 that is engageable with pin 56 in the fixed and/or locking state. Pegs 66, 68 are configured for frictional engagement with projection 76 and disposal within slot 74. Projection 76 includes a tapered cantilever and/or a tapered configuration, indicated by lines G in FIG. 8 where surfaces of projection 76 are angled. The tapered configuration of projection 76 and the tapered configuration of pegs 66, 68, indicated by lines H in FIG. 9 form a taper when angled surfaces of projection 76 frictionally engage with angled surfaces of pegs 66, 68 to rigidly connect pin 56 with slot 74. The taper between projection 76 and pegs 66, 68 reduces play/resist relative movement between slot 74 and pin 56 when navigation component 30 is in the non-movable, fixed and/or locking state, which increases accurate positioning of navigation component 30 relative to implant 100. In some embodiments, projection 76 and pegs 66, 68 can form a dual taper.

In some embodiments, the rigid connection between projection 76, pegs 66, 68 and spring 52 resists axial movement along axis X of shaft 14, as shown by arrows AA in FIG. 12. In some embodiments, the rigid connection between projection 76 and pegs 66, 68 resists tangential movement around shaft 14, as shown by arrows BB in FIG. 12. In some embodiments, the rigid connection between projection 76, pegs 66, 68, the fit between a diameter of surface 70 and an inner diameter of actuator 40, resists radial movement in and out of shaft 14, as shown by arrows CC in FIG. 12. In some embodiments, projection 76 may include alternate cross section configurations, for example, oval, oblong, triangular, square, hexagonal, polygonal, irregular, uniform, non-uniform and/or tapered.

Slot 78 is configured for engagement with pin 56 in the fixed and/or locking state, as shown in FIG. 11. Wall 72 defines a projection 79, similar to projection 76, disposed in slot 78. Projection 79 is frictionally engageable with pegs 66, 68 to form a rigid connection, similar to the rigid connection described above with regard to projection 76. In some embodiments, slot 78 is variously configured, for example, smooth, rough, arcuate, undulating, mesh, porous, semi-porous, dimpled and/or textured. In some embodiments, slot 78 may include alternate cross section configurations, for example, oval, oblong, triangular, square, hexagonal, polygonal, irregular, uniform, non-uniform and/or tapered.

As described herein, slot 80 is configured to connect slot 74 and slot 78, as shown in FIGS. 8-11. Pin 56 via pegs 66, 68 is configured to translate between the movable, non-fixed and/or non-locking state of slot 80 to the non-movable, fixed and/or locking state of slots 74 and 78. In some embodiments, slot 80 is variously configured, for example, smooth, rough, arcuate, undulating, mesh, porous, semi-porous, dimpled and/or textured.

To rotate navigation component 30 from slot 74 on the left side L of inserter 12 to slot 78 on the right side R of inserter 12, button 46 is manually engaged by a user, in a direction shown by arrow A in FIG. 6. Downward force from engaging button 46 causes spring 52 to be placed in an unexpanded configuration. Button 46 and spring 52 engage with pin 56 such that pin 56 translates, in the direction shown by arrow A, and pegs 66, 68 disengage from projection 76 and slot 74. Navigation component 30 is rotated manually by the user, in a direction shown by arrow B in FIG. 1. As navigation component 30 is rotated, pegs 66, 68 translate through slot 80. Navigation component 30 is further rotated, in the direction shown by arrow B in FIG. 1, and pegs 66, 68 are translated through slot 80 and into slot 78. Button 46 is released by the user, in a direction shown by arrow C in FIG. 6, and spring 52 is disposed in an expanded position. Spring 52 applies a force to button 46 such that button 46 is resiliently biased, translating pin 56, in the direction shown by arrow C. Angled surfaces of projection 79 frictionally engage with angled surfaces of pegs 66, 68 and pin 56 translates into slot 78, in a direction shown by arrow D in FIG. 11, to rigidly connect pin 56 with slot 78. In some embodiments, navigation component 30 is rotated 180 degrees from slot 74 to slot 78.

In some embodiments, the orientation of button 46 can be inverted or reversed and manually engaged by a user on an underside of actuator 40. In some embodiments, button 46 is disposed with handle 32 such that the user maintains tactile contact with inserter 12 via handle 32 and the user's hand when rotating navigation component 30. In some embodiments, a spring biased on/off button 46 is employed such that when button 46 is manually engaged, button 46 disengages navigation component 30 and forces navigation component 30 to rotate, enabling the user to change the position of navigation component 30 using only one hand, including, for example, the hand that is in contact with inserter 12.

In some embodiments, inserter 12 includes prongs, including, for example, two prongs configured to be slidable relative to shaft 14. When implant 100 is attached to end 16 in a selected direction/orientation, the prongs slidably engage with ramps within navigation component 30, pushing the ramps to bias navigation component 30 into a selected and/or aligned orientation, for example, the left side L or the right side R of inserter 12. In some embodiments, navigation component 30 is centrally disposed on shaft 14 and includes springs to return navigation component 30 to its centrally disposed location on shaft 14, thereby facilitating the orientation of navigation component 30 on the left side L or the right side R of inserter 12 as the prongs, described above, slide back and forth relative to shaft 14. In some embodiments, one prong orients navigation component 30 to the left side L of inserter 12 and one prong orients navigation component 30 to the right side R of inserter 12. In some embodiments, navigation component 30 orientation relative to the prongs indicates a direction with which implant 100 is loaded thereby removing user error with matching navigation component 30 orientation/position and implant 100 orientation.

Figure 13:
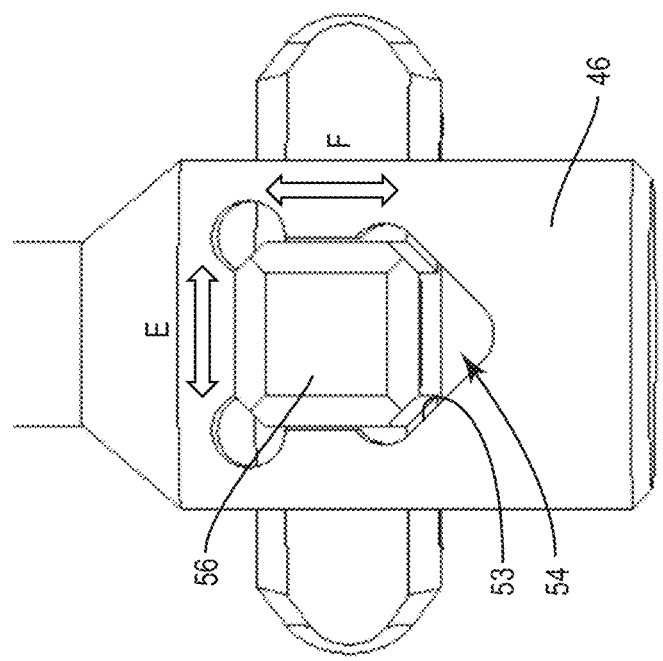
FIG. 13 is a break away plan view of components of one embodiment of a surgical system in accordance with the principles of the present disclosure.

In some embodiments, button 46 disengages pin 56 and pin 56 is configured to move or float within button 46 to facilitate relative movement, as shown by arrows E and F in FIG. 13. In some embodiments, button 46 engages with pin 56, such that the spring force of spring 52/button 46 causes angled faces 82 of button 46 to frictionally engage pin 56 to eliminate play/resist relative movement, as shown by arrows DD in FIG. 14. In some embodiments, faces 82 are angled at 45 degrees.

In some embodiments wall 72 defines a plurality of slots to facilitate a plurality of non-movable, fixed and/or locking states disposed about the circumference C of shaft 14 for positioning and alignment of navigation component 30 relative to sensor array 202 and/or relative to shaft 14. In some embodiments, shaft 14 includes 2 to 10 slots. In some embodiments, navigation component 30 rotates about a ball (not shown) disposed on shaft 14 such that navigation component 30 can be disposed about the circumference C of shaft 14 for positioning and alignment of navigation component 30 relative to sensor array 202.

Figure 16:
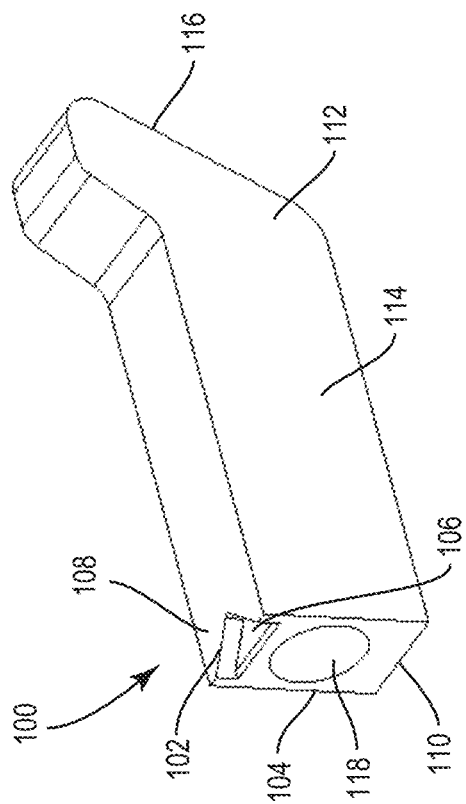
FIG. 16 is a perspective view of components of one embodiment of a surgical system in accordance with the principles of the present disclosure.
Figure 15:
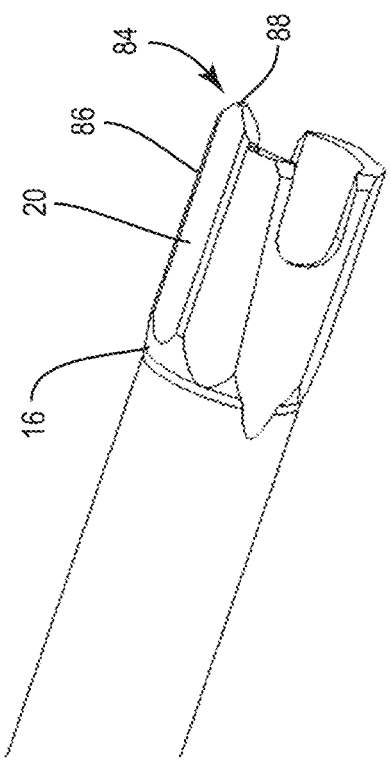
FIG. 15 is a break away perspective view of components of one embodiment of a surgical system in accordance with the principles of the present disclosure.

End 16 includes engagement portion 20 that includes a mating surface 84 configured for dedicated engagement with a mating surface 102 of an end 104 of implant 100, as shown in FIGS. 1, 15 and 16. End 16 engages end 104 in only one orientation via surfaces 84, 102. Surface 84 is disposed on a side 86 of portion 20 and includes a protrusion 88 configured for engagement with a corresponding groove 106 defined by surface 102 and disposed on a side 108 of end 104. Groove 106 has a dedicated and/or specific mating configuration with protrusion 88 and groove 106 engages protrusion 88 for mated engagement. Protrusion 88 and groove 106 are configured to prevent incorrect and/or non-selected engagement between end 20 and implant 100. If a user attempts to engage end 16 with implant 100 in error, an incorrect orientation and/or a non-selected implant, protrusion 88 engages a non-dedicated and/or non-specific mating surface, for example, a side of implant 100 that does not include groove 106, and as such, mating engagement between end 16 and implant 100 is prevented.

Protrusion 88 is wedge shaped and corresponding groove 106 is wedge shaped for mating engagement. In some embodiments, protrusion 88 and groove 106 are configured for releasable locked engagement. In some embodiments, protrusion 88 and groove 106 are variously shaped, for example, triangular, scalene triangle, right triangle, pyramidal, square, circular, oval, rectangular, pentagonal, hexagonal, heptagonal, octagonal, nonagon, parallelogram, rhombus, U-shaped, V-shaped, W-shaped, concave, crescent, heart, cross, arrow, cube, cylinder, star, a wavy line, semi-circular, ring, quatrefoil shaped or a combination thereof. In some embodiments, the shape can be regular, irregular and/or freeform. In some embodiments, protrusion 88 and groove 106 are variously configured, for example, smooth, rough, arcuate, undulating, mesh, porous, semi-porous, dimpled and/or textured.

Figure 18:
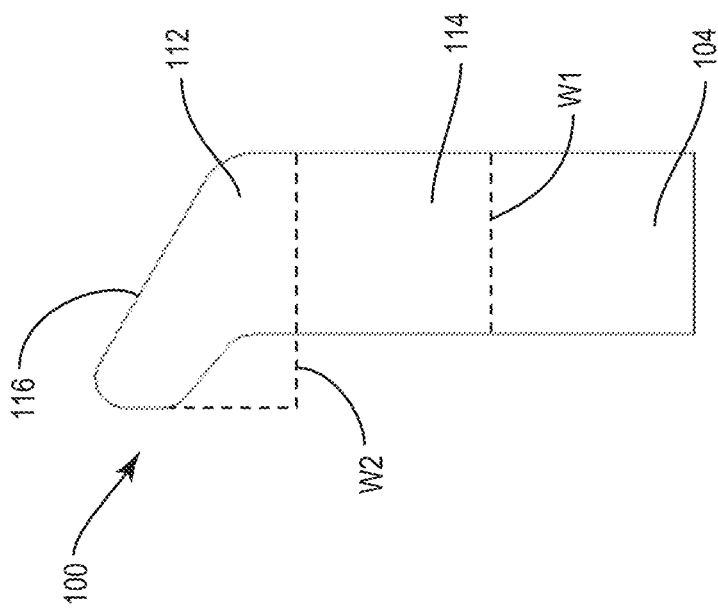
FIG. 18 is a plan view of the components shown in FIG. 16.
Figure 17:
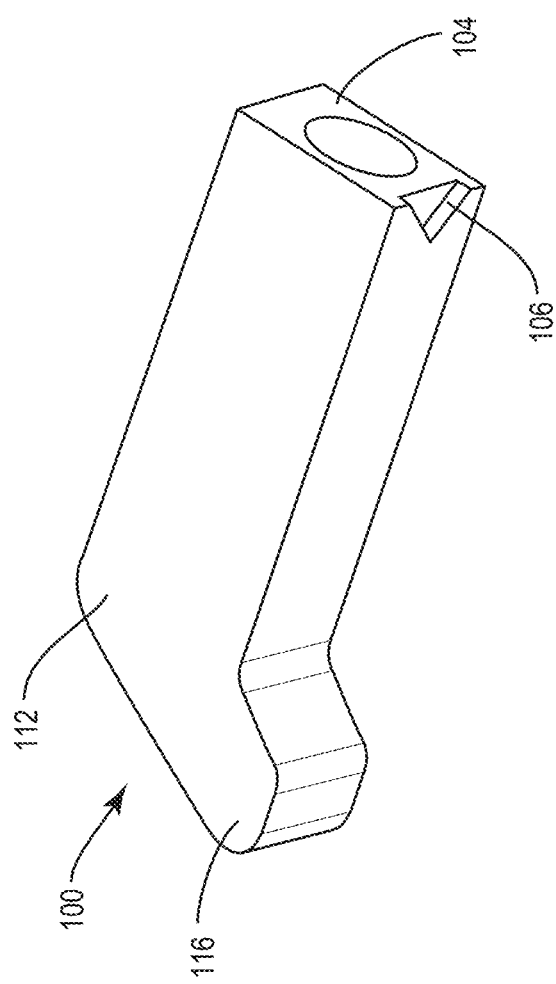
FIG. 17 is a perspective view of the components shown in FIG. 16.
Figure 20:
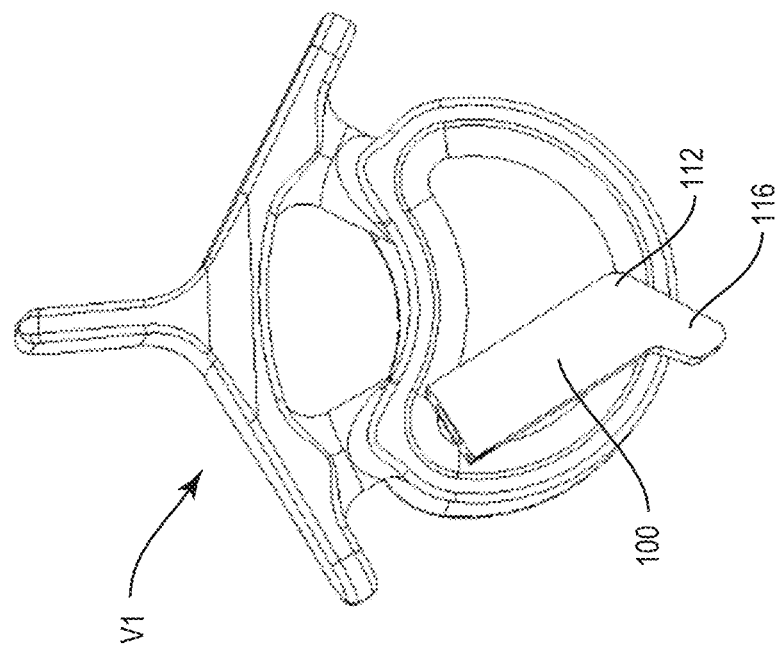
FIG. 20 is a perspective view of components of one embodiment of a surgical system in accordance with the principles of the present disclosure disposed with vertebrae.
Figure 19:
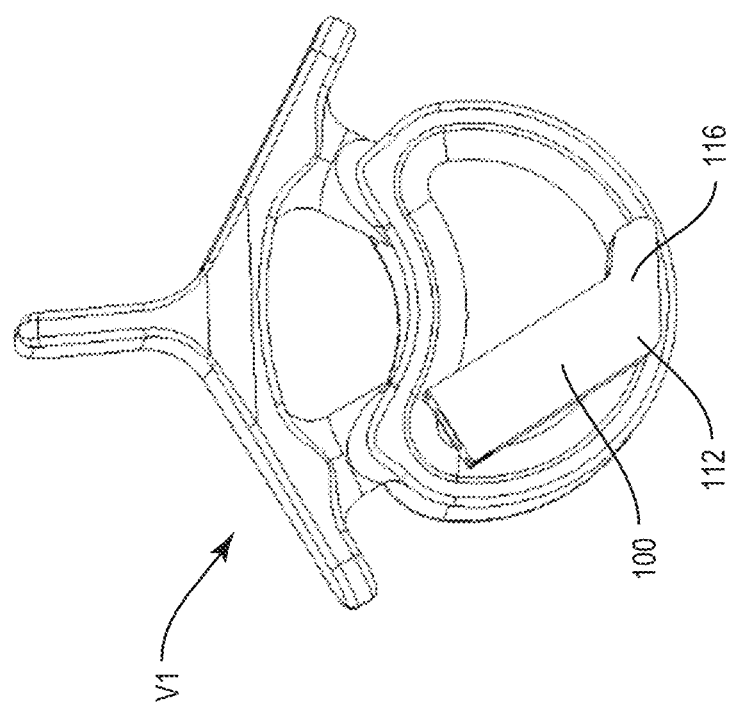
FIG. 19 is a perspective view of components of one embodiment of a surgical system in accordance with the principles of the present disclosure disposed with vertebrae.

Implant 100 extends between end 104 and an end 112, and a body 114 is disposed therebetween, as shown in FIGS. 16-18. Body 114 includes a width W1. End 112 includes a tip, for example, a sloped or biased tip 116. Tip 116 extends at an angle relative to body 114 and includes a width W2. Tip 116 protrudes relative to body 114 and width W2 is greater than width W1. In some embodiments, tip 116 avoids inserting implant 100 into a surgical space in an incorrect and/or non-selected orientation, for example, an intervertebral disc space V1 with tip 116 pointing in the incorrect direction and end 112 of implant 100 projecting from a front of an intervertebral disc space and concentrating vertebral loading in non-desirable orientation, as shown in FIG. 20. In some embodiments, tip 116 facilitates disposal of tip 116 in a correct direction or selected orientation, for example, tip 116 including end 112 of implant 100 extending parallel to an anterior rim of an intervertebral disc V1 to distribute load on the spine, as shown in FIG. 19. In some embodiments, implant 100 is capable of expanding unilaterally.

In some embodiments, an inner sleeve (not shown) is disposed through a central axis of shaft 14 and is configured for threadable engagement with a hole 118 on end 104 of implant 100. In some embodiments, the inner sleeve is translated, rotated and/or tightened to draw implant 100 into a tight fixation with end 16, and protrusion 88 is configured to prevent rotation of inserter 12 and implant 100. In some embodiments, end 16 includes multiple prongs and/or protrusions and end 16 engages end 104 in only one orientation via surfaces 84, 102. In some embodiments, the multiple prongs and/or protrusions include a single prong that varies in size from the other prongs, for example, a smaller or larger size protrusion 88.

As described herein, navigation component 30 is connected with shaft 14. Inserter 12 is configured for disposal adjacent a surgical site such that navigation component 30 is oriented relative to sensor array 202 to facilitate communication between navigation component 30 and sensor array 202 during a surgical procedure. Navigation component 30 is configured to generate a signal representative of a position of implant 100 relative to inserter 12 and/or tissue. In some embodiments, navigation component 30 may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals.

In some embodiments, navigation component 30 is dual sided, including, for example, a first side that is oriented relative to sensor array 202 and a second side that is oriented away from sensor array 202. In some embodiments, the dual sided navigation component 30 can communicate with two sensor arrays during the same procedure. In some embodiments, the first side represents implant 100 position and the second side represents the expansion amount.

Figure 24:
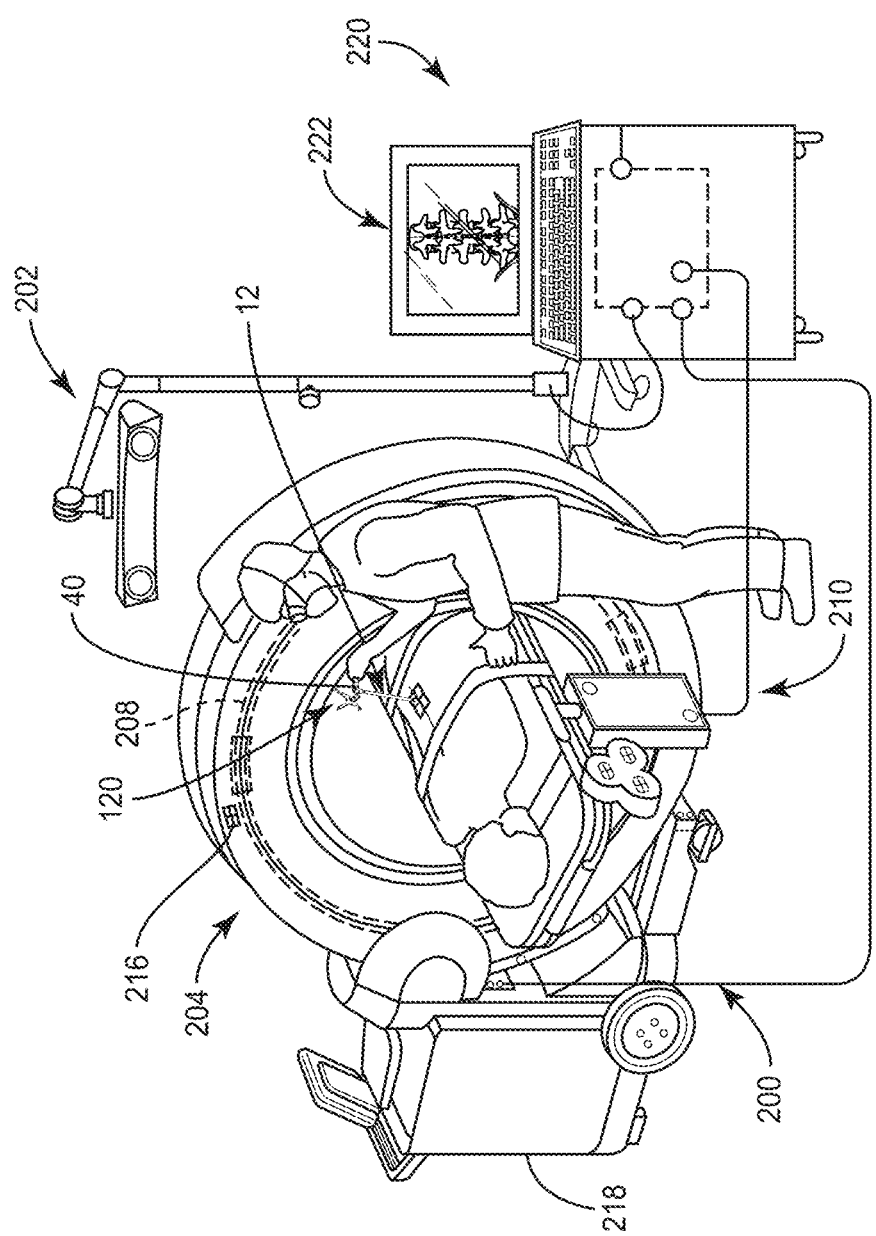
FIG. 24 is a perspective view of components of one embodiment of a surgical system in accordance with the principles of the present disclosure.

Navigation component 30 includes an emitter array 120. Emitter array 120 is configured for generating a signal to sensor array 202 of surgical navigation system 200, as shown in FIG. 24 and described herein. In some embodiments, the signal generated by emitter array 120 represents a position of implant 100 relative to inserter 12 and relative to tissue, for example, bone. In some embodiments, the signal generated by emitter array 120 represents a three dimensional position of implant 100 relative to tissue.

In some embodiments, sensor array 202 receives signals from emitter array 120 to provide a three-dimensional spatial position and/or a trajectory of implant 100 relative to inserter 12 and/or tissue. Emitter array 120 communicates with a processor of computer 220 of navigation system 200 to generate data for display of an image on monitor 222, as described herein. In some embodiments, sensor array 202 receives signals from emitter array 120 to provide a visual representation of a position of implant 100 relative to inserter 12 and/or tissue. See, for example, similar surgical navigation components and their use as described in U.S. Pat. Nos. 6,021,343, 6,725,080, 6,796,988, the entire contents of each of these references being incorporated by reference herein.

Surgical navigation system 200 is configured for acquiring and displaying medical imaging, for example, x-ray images appropriate for a given surgical procedure. In some embodiments, pre-acquired images of a patient are collected. In some embodiments, surgical navigation system 200 can include an O-arm® imaging device 204 sold by Medtronic Navigation, Inc. having a place of business in Louisville, Colo., USA. Imaging device 204 may have a generally annular gantry housing that encloses an image capturing portion 208.

In some embodiments, navigation system 200 comprises image capturing portion 208 that may include an x-ray source or emission portion and an x-ray receiving or image receiving portion located generally or as practically possible 180 degrees from each other and mounted on a rotor (not shown) relative to a track of image capturing portion 208. Image capturing portion 208 can be operable to rotate 360 degrees during image acquisition. Image capturing portion 208 may rotate around a central point or axis, allowing image data of the patient to be acquired from multiple directions or in multiple planes. Surgical navigation system 200 can include those disclosed in U.S. Pat. Nos. 8,842,893; 7,188,998; 7,108,421; 7,106,825; 7,001,045; and 6,940,941; the entire contents of each of these references being incorporated by reference herein.

In some embodiments, surgical navigation system 200 can include C-arm fluoroscopic imaging systems, which can generate three-dimensional views of a patient. The position of image capturing portion 208 can be precisely known relative to any other portion of imaging device 204 of navigation system 200. In some embodiments, a precise knowledge of the position of image capturing portion 208 can be used in conjunction with a tracking system 210 to determine the position of image capturing portion 208 and the image data relative to the patient.

Tracking system 210 can include various portions that are associated or included with surgical navigation system 200. In some embodiments, tracking system 210 can also include a plurality of types of tracking systems, for example, an optical tracking system that includes an optical localizer, for example, sensor array 202 and/or an EM tracking system that can include an EM localizer. Various tracking devices can be tracked with tracking system 210 and the information can be used by surgical navigation system 200 to allow for a display of a position of an item, for example, a patient tracking device, an imaging device tracking device 216, and an instrument tracking device, for example, emitter array 120, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted to a computer 218 where they may be forwarded to computer 220. Image transfer may be performed over a standard video connection or a digital link including wired and wireless. Computer 220 provides the ability to display, via monitor 222, as well as save, digitally manipulate, or print a hard copy of the received images. In some embodiments, images may also be displayed to the surgeon through a heads-up display.

In some embodiments, surgical navigation system 200 provides for real-time tracking of the position of implant 100 relative to inserter 12 and/or tissue. Sensor array 202 is located in such a manner to provide a clear line of sight with emitter array 120, as described herein. In some embodiments, fiducial markers 122 of emitter array 120 communicate with sensor array 202 via infrared technology. Sensor array 202 is coupled to computer 220, which may be programmed with software modules that analyze signals transmitted by sensor array 202 to determine the position of each object in a detector space.

Figure 21:
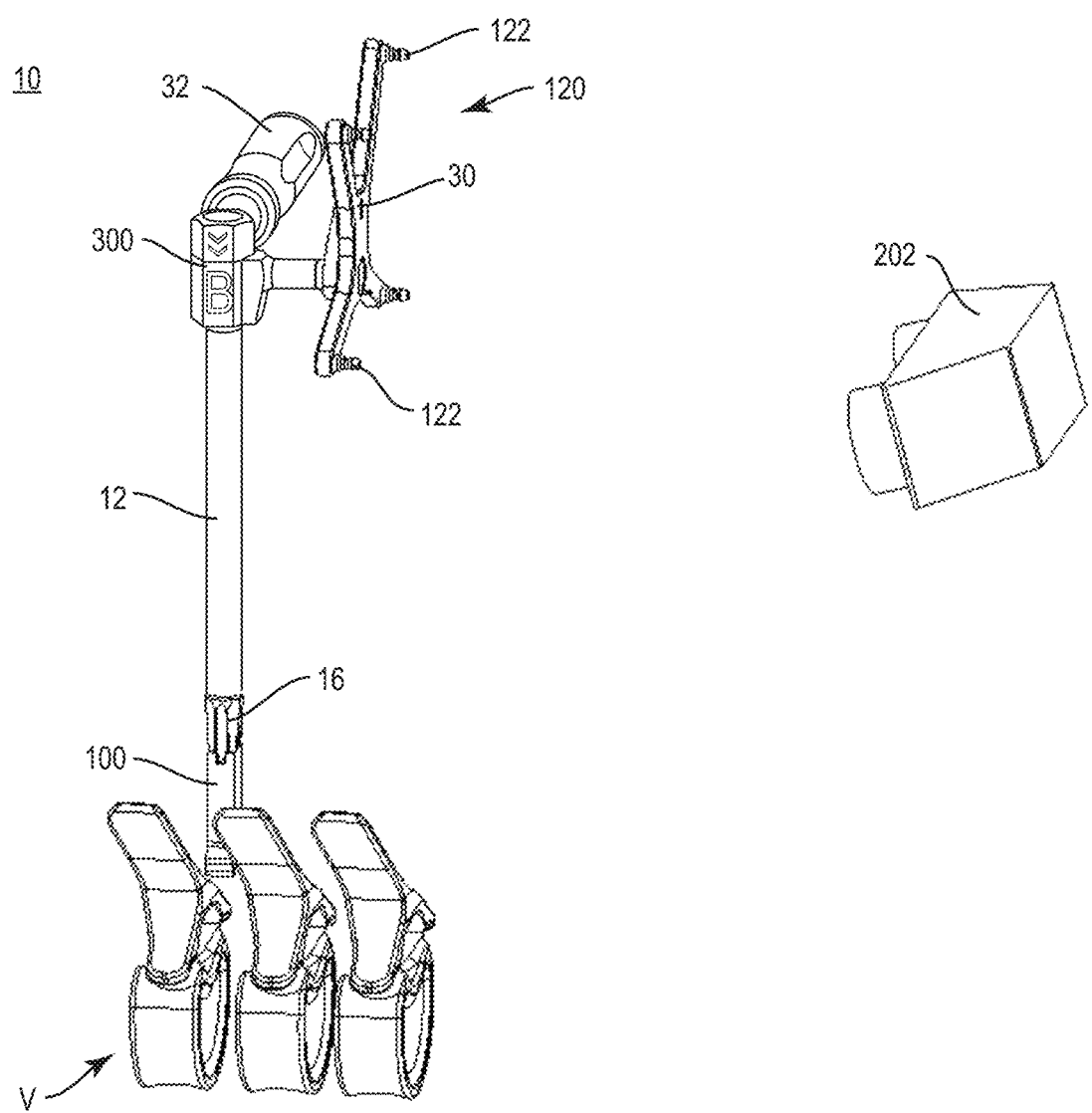
FIG. 21 is a perspective view of components of one embodiment of a surgical system in accordance with the principles of the present disclosure disposed with vertebrae.
Figure 23:
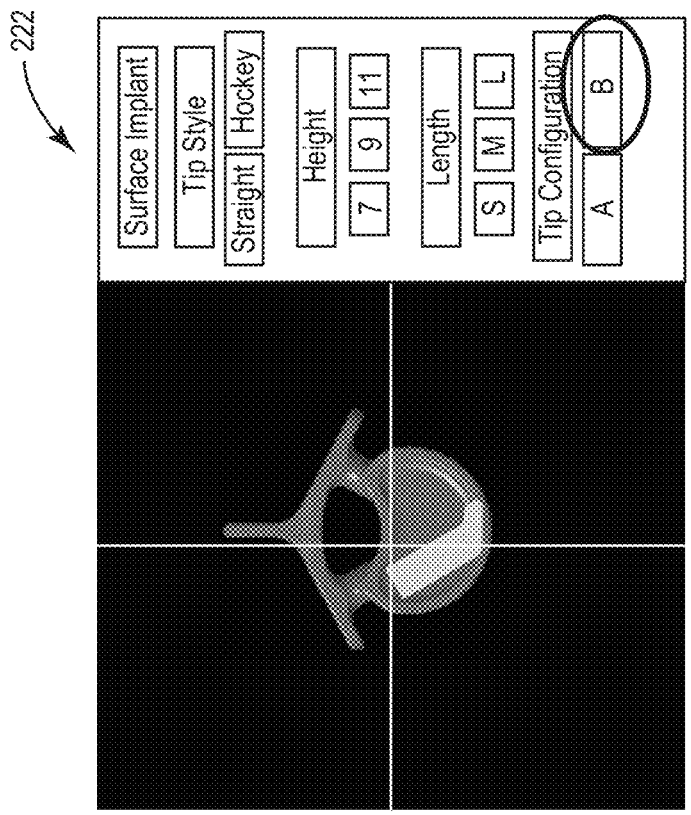
FIG. 23 is a graphical representation of a computer display of components of one embodiment of a surgical system in accordance with the principles of the present disclosure disposed with vertebrae.
Figure 22:
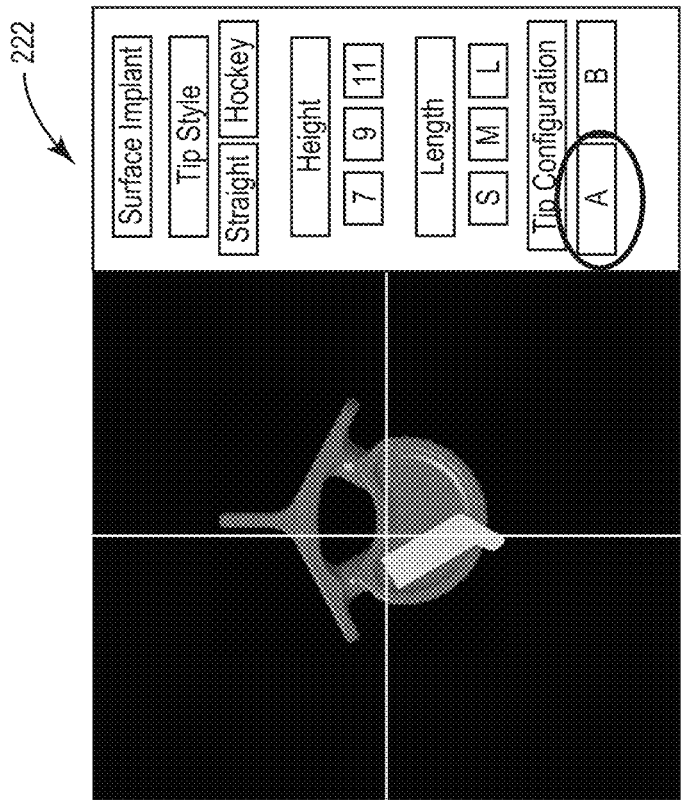
FIG. 22 is a graphical representation of a computer display of components of one embodiment of a surgical system in accordance with the principles of the present disclosure disposed with vertebrae.

In some embodiments, the processor of computer 220 of navigation system 200 executes a software program that includes an implant tip configuration menu that is displayed on monitor 222, as shown in FIGS. 22 and 23. The implant tip configuration menu allows a user to select a tip of inserter 12, and the processor communicates with monitor 222 to indicate the actual tip being implemented by inserter 12. In some embodiments, inserter 12 includes indicia 300, for example, a letter, number and/or shape, which indicates the type of implant orientation being employed, including for example, a left side L (e.g., letter A) or a right side R (e.g., letter B) orientation, as shown in FIG. 21. In some embodiments, the processor communicates with monitor 222 and implements the same indicia 300 used on inserter 12 such that inserter 12 indicia 300 and indicia displayed on monitor 222 match. In some embodiments, the processor and monitor 222 are coordinated with a direction of navigation component 30. In some embodiments, the processor and monitor 222 include a surface implant menu that includes a tip style, height of implant, length of implant and/or tip configuration. In some embodiments, surgical system 10 can include a second emitter array 120 to allow the software program to recognize which side, for example the left side L or the right side R of inserter 12 navigation component 30 is located on.

In some embodiments, the software program provides feedback to the user when navigation component 30 is the incorrect orientation. In some embodiments, the user, including, for example, surgical staff can set the software program menu according to indicia 300, for example, a letter shown when navigation component 30 and sensor array 202 are correctly aligned and/or oriented, as shown in FIGS. 22 and 23.

In assembly, operation and use, surgical system 10, similar to the systems and methods described herein, is employed with a surgical procedure for treatment of a spinal disorder affecting a section of a spine of a patient, as discussed herein. For example, the components of surgical system 10 can be used with a surgical procedure for treatment of a condition or injury of an affected section of the spine including vertebrae V, as shown in FIGS. 2 and 24. In some embodiments, one or all of the components of surgical system 10 can be delivered or implanted as a pre-assembled device or can be assembled in situ. Surgical system 10 may be completely or partially revised, removed or replaced.

The components of surgical system 10 can be employed with a surgical treatment of an applicable condition or injury of an affected section of a spinal column and adjacent areas within a body, for example, vertebrae. In some embodiments, the components of surgical system 10 may be employed with one or a plurality of vertebra. To treat a selected section of vertebrae V, a medical practitioner obtains access to a surgical site including vertebrae in any appropriate manner, such as through incision and retraction of tissues. In some embodiments, the components of surgical system 10 can be used in any existing surgical method or technique including open surgery, mini-open surgery, minimally invasive surgery and percutaneous surgical implantation, whereby vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for delivery of components of surgical system 10 including inserter 12 and implant 100, as described herein, adjacent an area within the patient's body, for example, vertebrae. In some embodiments, a preparation instrument (not shown) can be employed to prepare tissue surfaces of vertebrae, as well as for aspiration and irrigation of a surgical region.

Inserter 12 is connected with implant 100, as described herein, for disposal in an insertion or delivery orientation, as described herein. Navigation component 30 is initially disposed in a non-movable, fixed and/or locking state with shaft 14, for example, on the left side L of inserter 12. Navigation component 30 is adjustable and rotatable relative to shaft 14 such that navigation component 30 can be placed in non-movable, fixed and/or locking states about the circumference C of shaft 14 to orient navigation component 30 relative to sensor array 202 and/or other components of navigation system 200 to accommodate operating room setup.

To rotate navigation component 30 from slot 74 on the left side L of inserter 12 to slot 78 on the right side R of inserter 12, button 46 is manually engaged by a user, in a direction shown by arrow A in FIG. 6. Downward force from engaging button 46 causes spring 52 to be placed in an unexpanded configuration. Button 46 and spring 52 engage pin 56 such that pin 56 translates, in the direction shown by arrow A, and pegs 66, 68 disengage from projection 76 and slot 74. Navigation component 30 is rotated manually by the user, in a direction shown by arrow B in FIG. 1. As navigation component 30 is rotated, pegs 66, 68 translate through slot 80. Navigation component 30 is further rotated, in the direction shown by arrow B in FIG. 1, and pegs 66, 68 are translated through slot 80 and into slot 78. Button 46 is released by the user, in a direction shown by arrow C in FIG. 6, and spring 52 is disposed in an expanded position. Spring 52 applies a force to button 46 such that button 46 is resiliently biased, translating pin 56, in the direction shown by arrow C. Angled surfaces of projection 79 frictionally engage angled surfaces of pegs 66, 68 and pin 56 translates into slot 78, in a direction shown by arrow D in FIG. 11, to rigidly connect pin 56 with slot 78. Interbody implant 100 is disposed adjacent the surgical site.

During the surgery, the practitioner may reposition himself and/or inserter 12 relative to the patient and/or navigation system 200. During repositioning, navigation component 30 can be rotated, as described herein, to orient navigation component relative to sensor array 202. Rotation of navigation component 30 allows movement of the practitioner from one side of a surgical table to another side of the surgical table while maintaining a position of navigation component 30 relative to sensor array 202.

Inserter 12 is manipulated to deliver implant 100 to the vertebral space between vertebrae. Sensor array 202 receives signals from navigation component 30 to provide a three-dimensional spatial position and/or a trajectory of inserter 12 and/or implant 100 relative to the vertebral space between vertebrae and/or a depth of inserter 12 and/or implant 100 within the vertebral space for display on monitor 222. Inserter 12 is disengageable from interbody implant 100. In some embodiments, implant 100 provides height restoration between vertebral bodies, decompression, restoration of sagittal and/or coronal balance and/or resistance of subsidence into vertebral endplates.

In some embodiments, surgical system 10, as described herein, may include and/or be connected with various instruments including the configuration of the present disclosure, for example, inserters, extenders, reducers, spreaders, distractors, blades, retractors, clamps, forceps, elevators and drills, which may be alternately sized and dimensioned, and arranged as a kit.

In some embodiments, surgical system 10 includes an agent, which may be disposed, packed or layered within, on or about the components and/or surfaces of surgical system 10. In some embodiments, the agent may include bone growth promoting material, for example, bone graft to enhance fixation with vertebrae V. The components of surgical system 10 can be made of radiolucent materials such as polymers. Radiomarkers may be included for identification under x-ray, fluoroscopy, CT or other imaging techniques. In some embodiments, the agent may include one or a plurality of therapeutic agents and/or pharmacological agents for release, including sustained release, to treat, for example, pain, inflammation and degeneration. Upon completion of the procedure, the surgical instruments, assemblies and non-implanted components of surgical system 10 are removed from the surgical site and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a shaft connectable with a spinal implant, the shaft defining a slot;
   a navigation component connected with the shaft for orientation relative to a sensor to communicate a signal representative of a position of the spinal implant;
   an actuator comprising a button defining a cavity; and
   a pin disposed in the cavity and the slot, the pin being configured to move the navigation component relative to the shaft between a fixed position and a non-fixed position,
   wherein the fixed position includes a plurality of fixed positions of the navigation component with the shaft, the fixed positions being spaced about a circumference of the shaft.

2. The surgical instrument recited in claim 1, wherein the actuator comprises a spring disposed about the button.

3. The surgical instrument recited in claim 1, wherein the actuator comprises a spring configured to apply a force to the button to maintain the navigation component in the fixed position.

4. The surgical instrument recited in claim 3, wherein a force is applied to the button to overcome the force applied by the spring to cause the button to translate the navigation component into the non-fixed position.

5. The surgical instrument recited in claim 1, wherein the actuator comprises a spring configured to move between an expanded position in which the navigation component is in the fixed position and a non-expanded position in which the navigation component is in the non-fixed position.

6. The surgical instrument recited in claim 1, wherein the button is spring loaded to maintain the navigation component in the fixed position.

7. The surgical instrument recited in claim 1, wherein the cavity is transverse to a longitudinal axis defined by a length of the shaft.

8. The surgical instrument recited in claim 1, wherein a portion of an end of the pin is in flush engagement with an inner surface of the button to create a rigid fixation such that the button facilitates movement of the pin.

9. The surgical instrument recited in claim 1, wherein an end of the pin includes bifurcated arms.

10. The surgical instrument recited in claim 9, wherein the arms are disposed in a Y configuration.

11. The surgical instrument recited in claim 9, wherein the arms each include a surface that defines a peg, the pegs being angled relative to one another and configured for engagement with the shaft.

12. The surgical instrument recited in claim 11, wherein the pegs are in a tapered configuration relative to each other.

13. The surgical instrument recited in claim 1, wherein the pin includes opposite proximal and distal ends, a portion of the distal end being in flush engagement with an inner surface of the button to create a rigid fixation such that the button facilitates movement of the pin, the proximal end including bifurcated arms disposed in a Y configuration.

14. The surgical instrument recited in claim 1, wherein the slot includes a first transverse slot, a second transverse slot and a circumferential slot configured to connect the first and second transverse slots.

15. The surgical instrument recited in claim 14, wherein the second transverse slot is diametrically disposed about a circumference of the shaft relative to the first transverse slot.

16. The surgical instrument recited in claim 14, wherein the first and second transverse slots are configured for engagement with the pin to orient the navigation component in the non-fixed position on a left side and a right side of the shaft for alignment and detection of the signal with the sensor.

17. The surgical instrument recited in claim 1, wherein the shaft includes a projection disposed in the slot and engageable with the pin in the fixed position.

18. A surgical instrument comprising:
a shaft connectable with a spinal implant, the shaft defining a slot;
a navigation component connected with the shaft for orientation relative to a sensor to communicate a signal representative of a position of the spinal implant;
an actuator comprising a button defining a cavity; and
a pin disposed in the cavity and the slot, the pin being configured to move the navigation component relative to the shaft between a fixed position and a non-fixed position,
wherein the shaft includes a projection disposed in the slot and engageable with the pin in the fixed position,
wherein the slot includes a first transverse slot, a second transverse slot and a circumferential slot configured to connect the first and second transverse slots,
wherein the second transverse slot is diametrically disposed about a circumference of the shaft relative to the first transverse slot, and
wherein the first and second transverse slots are configured for engagement with the pin to orient the navigation component in the non-fixed position on a left side and a right side of the shaft for alignment and detection of the signal with the sensor.

19. A surgical instrument comprising:
a shaft connectable with a spinal implant, the shaft defining a slot;
a navigation component connected with the shaft for orientation relative to a sensor to communicate a signal representative of a position of the spinal implant;
an actuator comprising a button defining a cavity; and
a pin disposed in the cavity and the slot, the pin being configured to move the navigation component relative to the shaft between a fixed position and a non-fixed position,
wherein the cavity is transverse to a longitudinal axis defined by a length of the shaft.

20. The surgical instrument recited in claim 19, wherein a portion of an end of the pin is in flush engagement with an inner surface of the button to create a rigid fixation such that the button facilitates movement of the pin.

* * * * *